(12) United States Patent
Welke

(10) Patent No.: US 9,399,186 B2
(45) Date of Patent: Jul. 26, 2016

(54) FILTER SYSTEM FOR A BUILDING AND FILTER DEVICE

(71) Applicant: ZEOSYS-ZEOLITHSYSTEME-FORSCHUNGS-UND VERTRIEBSUNTERNEHMEN FÜR UMWELTSCHUTZ MEDIZIN-UND ENERGIETECHNIK, GMBH, Berlin (DE)

(72) Inventor: Hartmut Welke, Ahrensfelde (DE)

(73) Assignee: ZEOSYS-ZEOLITHSYSTEME-FORSCHUNGS-UND VERTRIEBSUNTERNEHMEN FÜR UMWELTSCHUTZ MEDIZIN-UND ENERGIETECHNIK GMBH (DE)

( * ) Notice: Subject to any disclaimer, the term of this patent is extended or adjusted under 35 U.S.C. 154(b) by 0 days.

(21) Appl. No.: 14/708,592

(22) Filed: May 11, 2015

(65) Prior Publication Data

US 2015/0336042 A1    Nov. 26, 2015

(30) Foreign Application Priority Data

May 21, 2014    (DE) ............... 20 2014 102 383 U

(51) Int. Cl.
| | |
|---|---|
| *B01D 46/44* | (2006.01) |
| *A61M 16/00* | (2006.01) |
| *B01D 53/04* | (2006.01) |
| *B01D 46/00* | (2006.01) |
| *B01D 46/42* | (2006.01) |
| *B01D 53/00* | (2006.01) |

(52) U.S. Cl.
CPC ......... *B01D 46/444* (2013.01); *A61M 16/0093* (2014.02); *B01D 46/0005* (2013.01); *B01D 46/0019* (2013.01); *B01D 46/4227* (2013.01); *B01D 53/00* (2013.01); *B01D 53/0415* (2013.01); *B01D 2253/102* (2013.01); *B01D 2253/1085* (2013.01); *B01D 2257/2064* (2013.01); *B01D 2257/2066* (2013.01); *B01D 2257/402* (2013.01); *B01D 2257/80* (2013.01); *B01D 2259/40084* (2013.01); *B01D 2259/41* (2013.01); *B01D 2259/4533* (2013.01); *Y02C 20/10* (2013.01)

(58) Field of Classification Search
CPC ....... B01D 46/10; B01D 46/18; B01D 24/007
USPC .......................................................... 96/397
See application file for complete search history.

(56) References Cited

U.S. PATENT DOCUMENTS 6,152,998 A * 11/2000 Taylor .................... B01D 46/18
                                                               55/354

(Continued)

*Primary Examiner* — Amber R Orlando
*Assistant Examiner* — Britanny Precht
(74) *Attorney, Agent, or Firm* — Schmeiser, Olsen & Watts, LLP

(57) ABSTRACT

A filter system for a building, in particular a hospital, having an exhaust air duct, by means of which a gas mixture is conducted out of the building, and a filter device, which is assigned to the exhaust air duct and is configured to filter at least partially anaesthetic gases out of the gas mixture flowing through the filter device is provided. A filter device for installation in a filter system is also provided.

8 Claims, 4 Drawing Sheets

(56) References Cited

U.S. PATENT DOCUMENTS

| | | | |
|---|---|---|---|
| 2001/0025640 A1* | 10/2001 | Pessala | A61M 16/009 128/205.27 |
| 2005/0150382 A1* | 7/2005 | Sheehan | B01D 46/0028 95/277 |
| 2007/0012188 A1* | 1/2007 | Tandon | B01D 46/0036 95/273 |
| 2009/0249954 A1 | 10/2009 | Gadkaree et al. | |
| 2012/0222556 A1 | 9/2012 | Filipovic | |
| 2013/0220330 A1 | 8/2013 | Hunt et al. | |

* cited by examiner

FILTER SYSTEM FOR A BUILDING AND FILTER DEVICE

CROSS-REFERENCE TO RELATED APPLICATIONS

This application claims priority to German Application No. 20 2014 102 383.6, having a filing date of May 21, 2014, the entire contents of which are hereby incorporated by reference.

FIELD OF TECHNOLOGY

The following relates to a filter system for a building, in particular a hospital, and to a filter device.

BACKGROUND

Filters for halogenated hydrocarbons (HKW) are known from the prior art. Activated carbons that act reactively are suitable for cleaning process or exhaust air. Such activated carbons are described in the documents DE 37 13 346 A1, DE 39 35 094 A1 and DE 40 03 668 A1. The prerequisites for high sorption capacity together with optimal regeneration ability are described in DD 239 947, DE 36 28 858 A1 and DE 37 31 688 A1.

Furthermore, it is known to use dealuminated zeolites adapted to the process as the sorbents, as described in DE 197 49 963 A1. The absorbed or adsorbed halogenated hydrocarbons are desorbed by heating, condensed and recovered. DE 101 18 768 A1 describes conservative regeneration with a steam carrier for a filter cartridge. Modified and/or dealuminated zeolites having a low water absorption of less than 2 percent by mass cause a reduction in the desorption temperature that conserves the sorbent and the sorbate.

In DE 10 2006 008 320 A1, a gas passage in the upper wall region of an individual filter insert is configured in such a manner that a plug flow is produced for the gases in this region, the breakthrough curves for inhalational anaesthetics being made more uniform. The anaesthetic gases used thus have "good" breakthrough curves at the upper edge of the filter insert with the hydrophobic zeolites, that is, with a steep and clear locally and chronologically determined characteristic of the transition, in that a sharp boundary is formed between the loaded and still unloaded parts of the zeolite filling. The filter system, which has a complex action, is confusing and allows best values for its chronological profile to be determined only after long-term, empirical experience in practice has been gained.

There is no shortage of tests to increase the loading of sorption beds for cleaning gas flows. In DE 43 19 327 A1, an untreated gas flow is conducted through two sorption beds successively. After the process has finished, the first sorption bed is regenerated and the flow direction is reversed so that the flow passes through the second bed first. However, the used sorbent is replaced by a freshly regenerated one in a laborious manner.

It is also known that an improvement in sorptive separation is made possible by physical difference, for example in the pore sizes and by modifications to the sorbent beds themselves. In the case of unequal gas components, as formed by the mixture portions of nitrous oxide and anaesthetic vapours in DE 197 06 806 A1, said gas components can be separated out selectively by different types of molecular screens.

In WO 2009/083275 A1, a first sorption bed with a hydrophobic molecular screen carbon is series-connected (consecutively) upstream of a second sorption bed with a hydrophobic zeolite. The two beds each form a process stage, and the sorptive flows through them in a spatially successive manner. The two stages have a common throughput parameter for the carrier gas, especially for air, and also steam for the regeneration agent during regeneration. These process variables are of course dependent on the gas pressure and temperature and on the volumetric flow of the carrier gas. The filter arrangement can operate continuously in a production or gas-cleaning system or else can be configured as a filter cartridge that is regenerated and evacuated as needed. Sorption from the carrier gas, in particular desorption into the carrier gas and distillation with saturated steam are combined with each other.

Despite the multiplicity of known filters and filter devices, anaesthetic gases in hospitals usually pass unfiltered into the open air via a central extraction system (pipeline) and contribute to environmental pollution.

SUMMARY

An aspect relates to technologies for cleaning the exhaust air of buildings.

According to one aspect, a filter system is provided for a building, in particular a hospital. The filter system has an exhaust air duct, by means of which a gas mixture is conducted out of the building. Furthermore, the filter system has a filter device, which is assigned to the exhaust air duct and is designed to filter at least partially anaesthetic gases out of the gas mixture flowing through the filter device. The filter device can be arranged in the exhaust air duct. Alternatively, the filter device can be arranged upstream or downstream of the exhaust air duct. The filter system can have a plurality of filter devices.

According to a further aspect, a filter device is provided for installation in a filter system.

The gas mixture can be for example air (that is, can contain nitrogen, oxygen, carbon dioxide and water vapour), to which one or more anaesthetic gases (inhalational anaesthetics) have been added. Examples of anaesthetic gases are nitrous oxide, sevoflurane, enflurane, isoflurane, halothane and desflurane. The filter device is designed to remove the anaesthetic gas(es) at least partially from the gas mixture.

The filter system is particularly suitable for installation in a hospital. Approximately 6 million litres of anaesthetic gases are currently released into the atmosphere. The filter system can be used to filter anaesthetic gases out of the air so that they do not pass into the environment. This reduces the greenhouse effect. Furthermore, the filtered anaesthetic gases can be recovered from the filter device and used again after processing.

It can be provided for air from several rooms in the building, for example operating theatres, to be collected and conducted out of the building through the exhaust air duct. The plurality of rooms can be connected with an anaesthetic gas conveying system. The possibility is created of filtering the exhaust air from several rooms with a central filter system.

The flow rate of the gas mixture through the filter device can be between 40 and 60 l/min.

The filter device can have one or more filters. The one or more filters can be filled at least partially with activated carbon and/or a zeolite. The activated carbon and/or the zeolite form a sorbent, to which the anaesthetic gas adsorbs. The sorbent can be microporous. Zeolites are crystalline aluminosilicates, which occur naturally in numerous forms, but can also be produced synthetically. For example, Si-rich (dealuminated) zeolites can be used as sorbents (filter material), preferably with an Si:Al ratio of greater than 180:1 (corresponds to an SiO$_2$:Al$_2$O$_3$ ratio of 360:1). A plurality of filters can be arranged one behind the other and/or one next to the other. A single row of several filters can be formed. Alternatively, a two dimensional (matrixlike) arrangement of filters can be provided, where for example two rows of four filters each are formed.

According to one embodiment, a first measuring device can be arranged upstream of the filter device, the first measuring device being configured to determine an amount of anaesthetic gas in the gas mixture flowing into the filter device. Furthermore, a second measuring device can be arranged downstream of the filter device, the second measuring device being configured to determine an amount of anaesthetic gas in the gas mixture flowing out of the filter device. Alternatively or additionally, the first and/or second measuring device can be configured to determine a concentration of anaesthetic gas in the gas mixture. The first and/or second measuring device can have a display device to display measurement results.

The filter system can furthermore have a control device, which is configured to adjust a number of filters through which the gas mixture passes as it flows through the filter device, depending on the amount of anaesthetic gas determined by means of the first measuring device. The control device can have a processor, a RAM, a storage medium and/or inputs and outputs for signals.

Each filter of the filter device can have a fill level measuring device, which is configured to determine and where necessary display a fill level of the respective filter with anaesthetic gas.

According to one development, the filter device can have a filter holder for holding one or more filters through which the gas mixture is to flow, a magazine for storing unused filters, and a store for receiving used filters. Used filters can be removed from the store and fed to a recovery device. New, unused filters can be introduced into the magazine. The filters can be taken out and put in while the filter system is running.

In a further embodiment, the filter system can have a changing device, the control device being further configured to transport a used filter from the filter holder into the store and an unused filter from the magazine into the filter holder by means of the changing device. The filters can be changed while the filter system is in operation.

The filter device can have for example a pre-filter for filtering particles and/or moisture out of the gas mixture. Dust and/or water vapour can thereby be removed from the gas mixture before the gas mixture enters the filter device. The filter device can furthermore have a collection container for holding the filtered water vapour.

BRIEF DESCRIPTION

Some of the embodiments will be described in detail, with reference to the following figures, wherein like designations denote like members, wherein.

DETAILED DESCRIPTION

The same reference symbols are used for the same components below.

Figure 1:
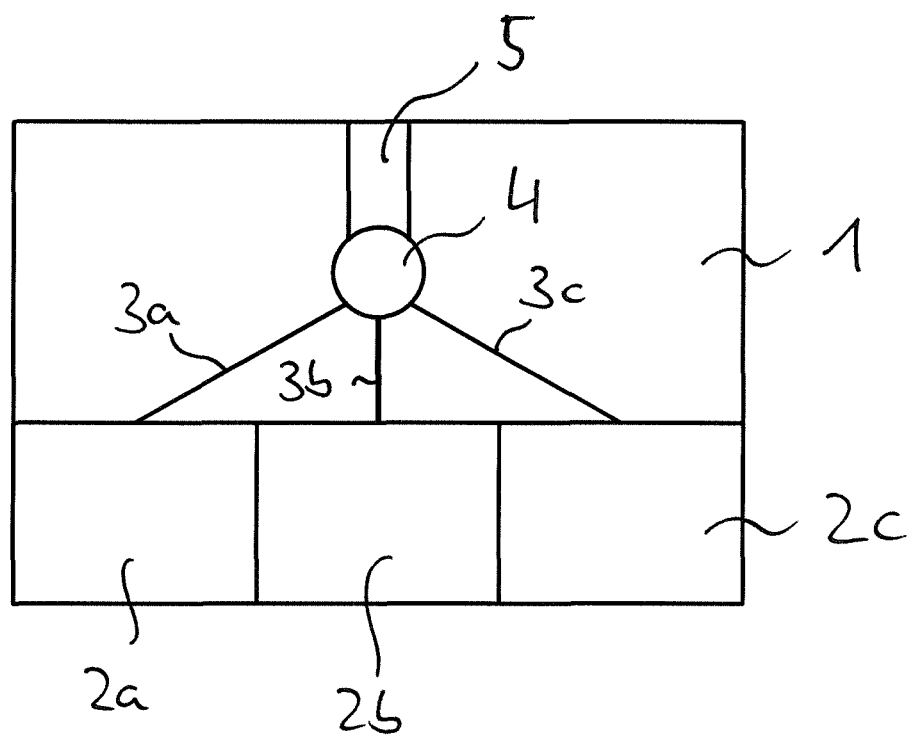
FIG. 1 shows a schematic illustration of a building with an embodiment of a filter system.

FIG. 1 schematically shows a building 1 having several rooms 2a, 2b, 2c. The air is extracted out of each room 2a, 2b, 2c and passes via pipelines 3a, 3b, 3c into a filter device 4. The filter device 4 is arranged upstream of a duct 5 and is designed to filter at least some anaesthetic gases out of the air. After the air has flowed through the filter device 4, it is cleaned of anaesthetic gases. The cleaned air leaves the building 1. The filter device 4 provides a central filter for the exhaust air from the rooms 2a, 2b, 2c.

Figure 2:
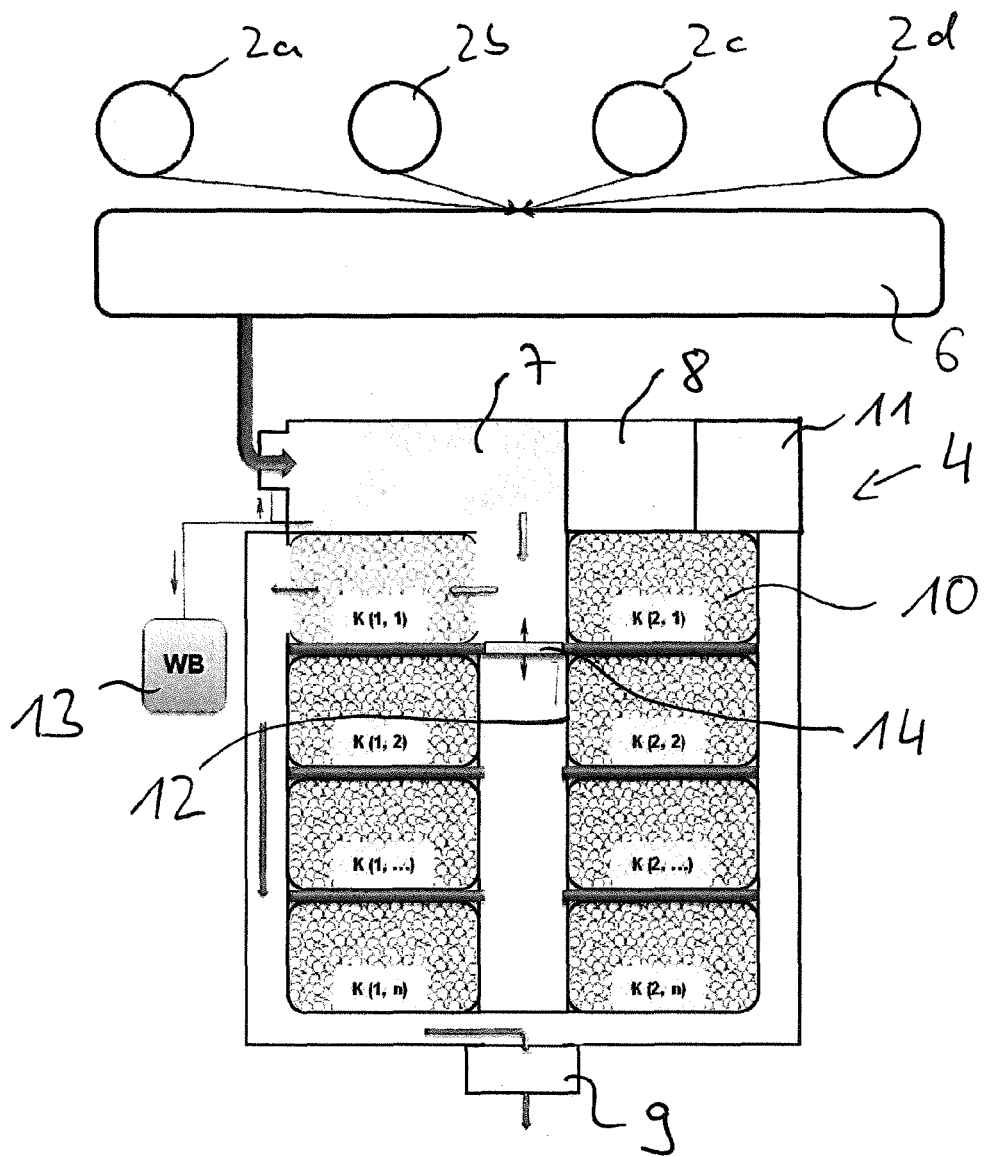
FIG. 2 shows an embodiment of the filter system with a filter device.

FIG. 2 shows an embodiment of a filter system. Air from the operating theatres 2a, 2b, 2c, 2d is collected by means of an anaesthetic gas conveying system 6. The air is a gas mixture, which contains nitrogen, oxygen, carbon dioxide, water vapour, and to which anaesthetic gas fractions are added. The air can also contain fine particles, for example dust. The air is conducted into the filter device 4. The air is first conducted through the pre-filter 7. The pre-filter 7 is used to filter particles and/or water vapour out of the air. The filtered water is collected in a container 13.

After the air has passed through the pre-filter 7, it is tested by means of a first gas sensor 8. The gas sensor 8 is configured to determine the amount and/or concentration of the anaesthetic gas(es) in the air. The measured values are transmitted to a control device 11. Depending on the determined measured values, the control device 11 determines how many filters 10 the air must flow through in order to obtain a predefined anaesthetic gas amount and/or concentration value in the air flowing out. The fill level of the filters can be taken into account during the calculation. The control device determines suitable settings for closure elements 12, 14, with which a path through the filter device can be set for the air. The closure element 14 is vertically adjustable. Furthermore, the closure elements 12 of the filters 10 can be opened or closed in order to allow or prevent air entering the respective filter. In the embodiment shown, the closure elements 12, 14 are set such that the air is conducted only through one filter (K(1,1)). Other combinations of the closure elements 12, 14 are possible to include further filters 10 in the cleaning process.

A second gas sensor 9 is arranged at an air outlet of the filter device 4. Said sensor determines the anaesthetic gas amount and/or concentration in the air flowing out of the filter device. The measured values can be transmitted to the control device 11 for checking. Depending on the measured values, the number of filters 10 through which flow passes can where necessary be adjusted in order to achieve a predefined measured value.

The filters 10 are filled with dealuminated zeolites or activated carbon, to which the anaesthetic gas adsorbs.

Figure 3:
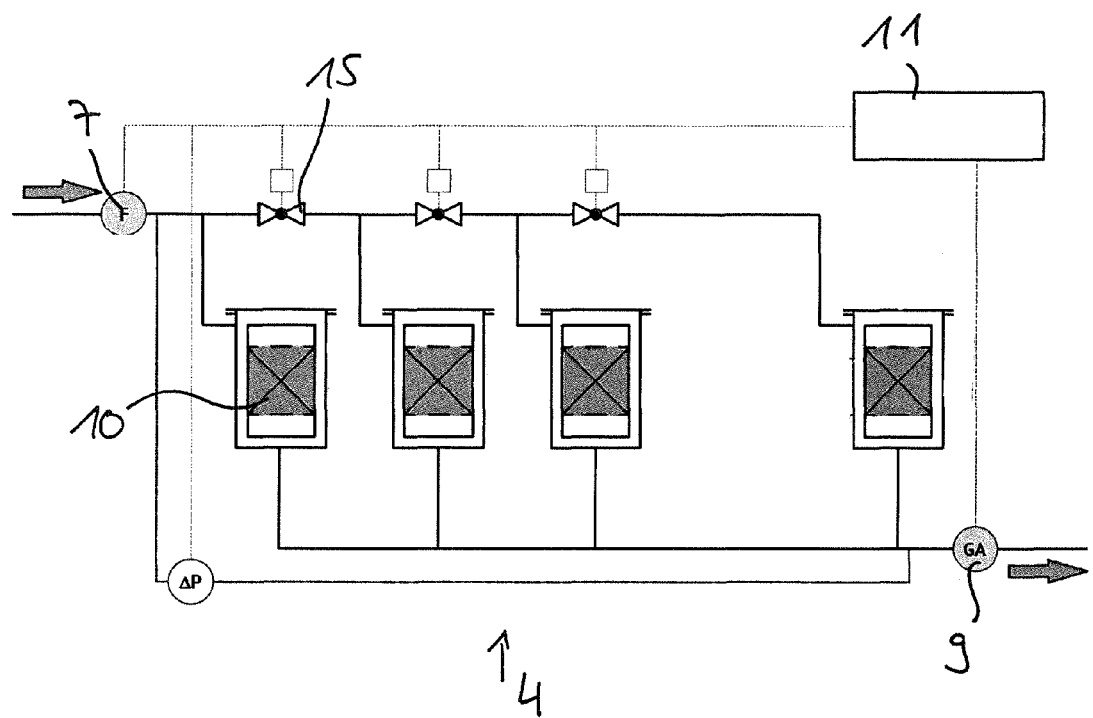
FIG. 3 shows a further embodiment of the filter device.

FIG. 3 shows a further embodiment of the filter device 4. A pre-filter 7, which removes dust and water first, is arranged at the inlet. The pre-filter 7 can be coupled to a gas sensor in order to determine the amount and/or concentration of anaesthetic gas. The values can then be transmitted to the control device 11.

Several filters 10 are arranged parallel to each other. The control device 11 determines (depending on the transmitted values) which valves 15 are opened or closed in order to set the number of filters through which air flows.

The second gas sensor 9 is provided at the outlet of the filter device 4 to check the gas mixture flowing out.

Figure 4:
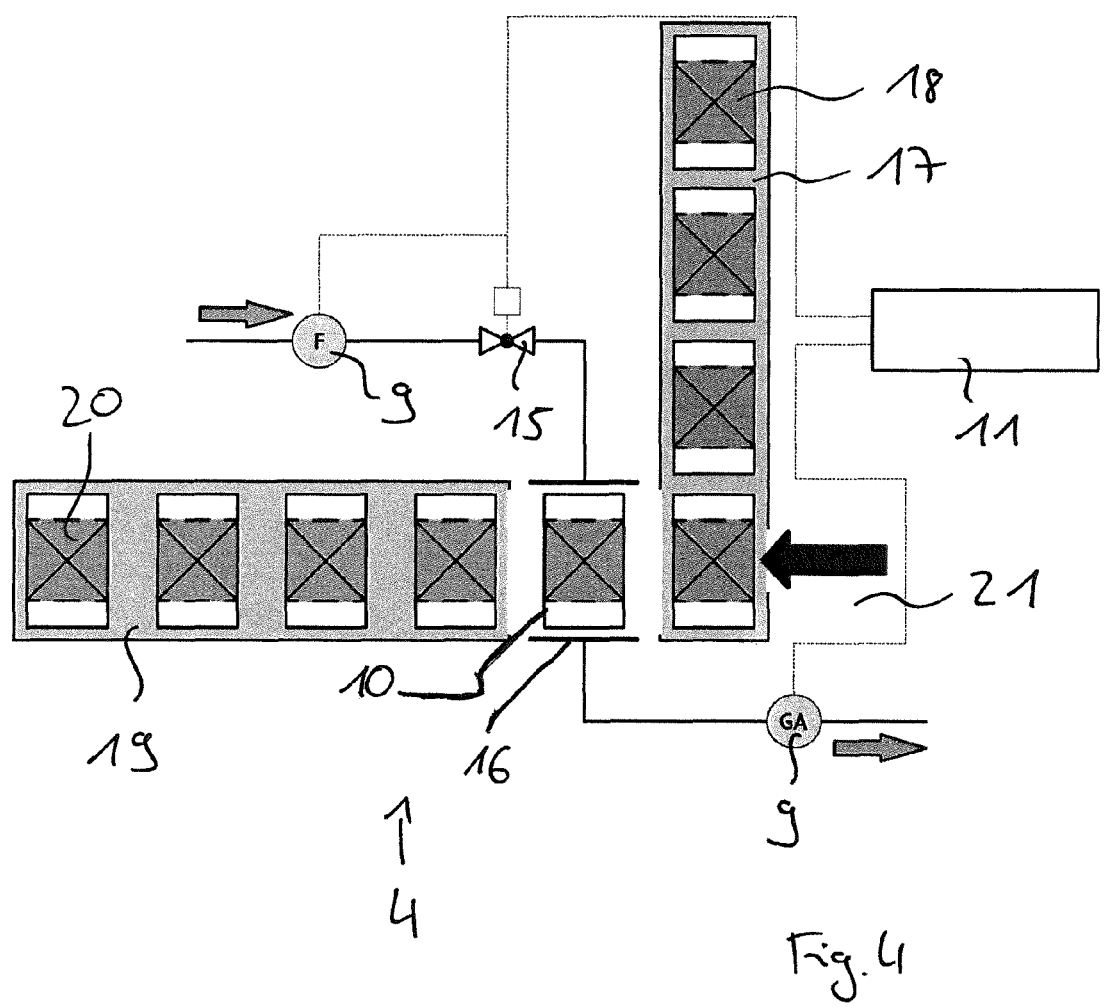
FIG. 4 shows a further development of the filter device.

FIG. 4 shows a further embodiment. Inflowing air is first cleaned of dust and water by the pre-filter 7. In this case too, the pre-filter 7 is formed with a gas sensor to analyse the gas mixture. Measured values on the amount and/or concentration of the anaesthetic gas are transmitted to the control device 11. The control device 11 regulates the valve 15 in order to set the air flow quantity.

The air flows through the filter 10. The filter 10 is arranged in a filter holder 16, which holds the filter 10 in the gas flow path. The filter 10 can also be referred to as an "active filter" in this embodiment. The filter device comprises a magazine 17 and a store 19. New, unused filters, which are used when the active filter 10 is full, are arranged in the magazine 17. All the filters are equipped with a fill level sensor (not shown). The data of the fill level sensor of the active filter 10 are sent to the control device. If the active filter 10 is full, a new filter 18 is brought from the magazine 17 into the filter holder by means of a changing device 21. The used filter 10 is transported into the store 19, where it is stored temporarily with other used filters 20. The used filters 20 can be removed from the store 19. They can be supplied to a regeneration process in order to recover the filtered anaesthetic gas. A method for recovering anaesthetic gases is described in WO 2009/083275 A1. New filters 18 can be supplied to the magazine. The active filter 10 is changed while the system is in operation.

The gas sensor 9, with which the gas mixture flowing out is checked for anaesthetic gas, is formed at the outlet of the filter device 4.

It is possible to combine the embodiments shown in FIGS. 3 and 4 such that each of the parallel filters is coupled to a magazine and a store as well as to a changing device.

The features disclosed in the description, claims and drawings can be relevant to the implementation of the invention both individually and in any combination.

The invention claimed is:

1. A filter system for a building, the filter system comprising:
   an exhaust air duct, by means of which a gas mixture is conducted out of the building; and
   a filter device, which is assigned to the exhaust air duct and is configured to filter at least partially anaesthetic gases out of the gas mixture flowing through the filter device, the filter device having one or more filters;
   wherein a first measuring device is arranged upstream of the filter device, the first measuring device configured to determine an amount of anaesthetic gas in the gas mixture flowing into the filter device;
   wherein the filter system further includes a control device configured to adjust a number of filters through which the gas mixture passes as the gas mixture flows through the filter device, depending on the amount of anaesthetic gas determined by means of the first measuring device.

2. The filter system according to claim 1, wherein each of the one or more filters of the filter device has a fill level measuring device, which is configured to determine a fill level of the respective filter with anaesthetic gas.

3. The filter system according to claim 1, wherein the filter device has a filter holder for holding the one or more filters through which the gas mixture is to flow, a magazine for storing unused filters and a store for receiving used filters.

4. The filter system according to claim 3, further comprising a changing device, wherein the control device is further configured to transport a used filter from the filter holder into the store and an unused filter from the magazine into the filter holder by means of the changing device.

5. The filter system according to claim 1, wherein a second measuring device is arranged downstream of the filter device, and the second measuring device is configured to determine an amount of anaesthetic gas in the gas mixture flowing out of the filter device.

6. The filter system according to claim 1, wherein the filter device has a pre-filter for filtering particles or moisture out of the gas mixture.

7. A filter device for installation in a filter system according to claim 1.

8. The filter system of claim 1, wherein the building is a hospital.

* * * * *